United States Patent [19]

Robinson et al.

[11] Patent Number: 5,001,282

[45] Date of Patent: Mar. 19, 1991

[54] METHOD OF TREATING DIABETES MELLITUS WITH BISPHENOL DERIVATIVES

[75] Inventors: Keith M. Robinson, Glendale; Simon J. T. Mao, Loveland; Roger A. Parker; Richard L. Jackson, both of Cincinnati, all of Ohio

[73] Assignee: Merrell Dow Pharmaceuticals Inc., Cincinnati, Ohio

[21] Appl. No.: 385,623

[22] Filed: Jul. 26, 1989

[51] Int. Cl.[5] ............................................. C07C 39/14
[52] U.S. Cl. ...................................... 568/730; 568/722
[58] Field of Search ................ 568/722, 730, 740, 799

[56] References Cited

U.S. PATENT DOCUMENTS

| | | | |
|---|---|---|---|
| 3,549,712 | 12/1970 | Hay et al. | 568/730 |
| 4,049,731 | 9/1977 | Restaino | 568/730 |
| 4,115,590 | 9/1978 | Lerner | 424/337 |
| 4,361,708 | 11/1982 | Strom | 568/730 |
| 4,410,736 | 10/1983 | Strom | 568/730 |

OTHER PUBLICATIONS

Brownlee and Cerami, *Annu. Rev. Biochem.* 50,385 (1981).
Bell and Hye, *J. Surg. Res.* 35,433 (1983).
Kharasch and Joshi, *J. Org. Chem.* 22, 1439 (1957).
Hart and Cassis, *J. Amer. Chem. Soc.* 73, 3179 (1951).
Pastor, *J. Org. Chem.* 49, 5260 (1984).

*Primary Examiner*—Werren B. Lone
*Attorney, Agent, or Firm*—Louis J. Wille

[57] ABSTRACT

The present invention relates to a method of lowering blood glucose in a patient afflicted with diabetes mellitus comprising administering to said patient a therapeutically effective glucose lowering amount of a 4,4'-bis(2,6-di-alkyl-phenol). The present invention also relates to a process for making 4,4'-bis(2,6-di-alkyl-phenol).

1 Claim, No Drawings

METHOD OF TREATING DIABETES MELLITUS WITH BISPHENOL DERIVATIVES

Diabetes mellitus is a disorder of carbohydrate metabolism characterized by hyperglycemia. In general, the hyperglycemia associated with diabetes mellitus is caused by absolute or relative insulin deficiency, or insulin resistance, or both.

Insulin is a hormone secreted by the β-cells of the islets of Langerhans in the pancreas. Insulin regulates glucose metabolism and promotes the transport of glucose from the blood to the skeletal muscle, adipose tissue, and other tissues so that it can be utilized as an energy source or stored as glycogen. Glucagon is a hormone secreted by the α-cells of the islets of Langerhans in the pancreas and generally has effects which counteract the effects of insulin.

Physiologic states in which there is an absolute or relative insulin deficiency, or insulin resistance, or both, result in disease states such as diabetes mellitus. An absolute insulin deficiency occurs when the pancreatic β-islet cells no longer secrete significant amounts of insulin. A relative insulin deficiency occurs where the ratio of glucagon to insulin secreted by the pancreas is consistently higher than that found in normal subjects. Insulin resistance can occur where there is impaired insulin action due to anti-insulin receptor antibodies, reduced insulin receptors or other receptor or post-receptor defects.

Diabetes mellitus can be classified as follows:
1. Insulin-dependent diabetes mellitus (also called type I diabetes);
2. Non-insulin-dependent diabetes mellitus (also called type II diabetes).

Patients with insulin-dependent diabetes mellitus (IDDM) have little or no endogenous insulin secretory capacity. These patients develop extreme hyperglycemia and are susceptible to developing ketosis and ketoacidosis. Patients with non-insulin-dependent diabetes mellitus (NIDDM) retain the ability to secrete insulin. However, this insulin secretion is at reduced levels or is overbalanced by excessive secretion of counteracting hormones such as glucagon. In either case there is a relative insulin deficiency. Patients with NIDDM also develop hyperglycemia but are not as susceptible to ketosis or ketoacidosis as those patients with IDDM.

In general, diabetes mellitus develops in response to damage to the insulin-secreting β-islet cells of the pancreas. This damage can result from primary diabetes mellitus, in which the β-islet cells are destroyed by the autoimmune system, or as a secondary diabetic response to other primary diseases, such as pancreatic disease, excesses of counterinsulin hormones, drug-induced conditions or genetic abnormalities other than that associated with primary diabetes. In either case, the β-islet cells cannot produce sufficient insulin to adequately transport the blood glucose from the blood to the insulin sensitive tissues.

Disease states such as diabetes mellitus therefore result in hyperglycemia (abnormally high levels of blood glucose), glycosuria (excessive excretion of glucose in the urine) and decreased glycogen levels in the liver, as well as other metabolic consequences. In addition to the metabolic consequences of the disease, there are also a number of degenerative complications of the disease which result from these metabolic consequences. For example, diabetic retinopathy, diabetic neuropathy, nephropathy, atherosclerosis, cardiomyopathy, dermopathy, diabetic foot syndrome and peripheral vascular disease are all complications associated with and resulting from diabetes mellitus. It is generally believed that these degenerative complications are caused by the metabolic consequences of the disease. It is also generally believed by those skilled in the art that reduction of the hyperglycemia associated with diabetes mellitus in particular will delay or prevent these degenerative complications in patients afflicted with diabetes mellitus [see Brownlee and Cerami, *Annu. Rev. Biochem.* 50, 385 (1981)]. Furthermore, in severe hyperglycemia, the blood glucose levels can become so high that hyperosmolar non-ketotic coma can result. Reduction of blood glucose levels in diabetic patients can thus prevent hyperosmolar non-ketotic coma resulting from hyperglycemia.

Some pharmacologically active agents, such as alloxan, can produce a drug-induced diabetic condition in animals. Alloxan, or mesoxalylurea, selectively destroys the capacity of the β-islet cells of the pancreas to produce insulin. Alloxan-treated animals retain very little or no endogenous insulin secretory capacity and develop hyperglycemia in a manner similar to that in IDDM. As such, alloxan-treated animals provide a standard experimental model for diabetes mellitus in man which is well known and appreciated by those skilled in the art [see R. H. Bell and R. J. Hye, *J. Surg. Res.* 35: 433-60 (1983)]. The effect of experimental agents on the hyperglycemia of the alloxan-treated animals can thus be studied to determine whether these agents reduce the hyperglycemia associated with the experimental diabetes. Positive results in this experimental model are well known and appreciated to be reasonably predictive of results in humans with diabetes mellitus.

The present invention provides a method of lowering blood glucose in a patient afflicted with diabetes mellitus comprising administering to said patient a therapeutically effective glucose lowering amount of a compound of formula (1)

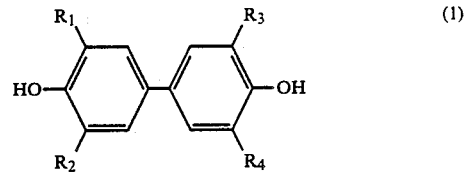

wherein $R_1$, $R_2$, $R_3$ and $R_4$ are each independently a $C_1$–$C_6$ alkyl group. The present invention further provides a method of treating a patient afflicted with diabetes mellitus comprising administering to said patient a therapeutically effective glucose lowering amount of a compound of formula (1). The present invention thus provides a means for lowering blood glucose and thereby delaying or preventing the diabetic complications resulting from hyperglycemia associated with diabetes mellitus.

As used herein, the term "$C_1$–$C_6$ alkyl group" means and includes saturated alkyl groups of straight, cyclic or branched-chain configuration made up of from one to six carbon atoms. Included within the scope of this term are methyl, ethyl, n-propyl, isopropyl, n-butyl, isobutyl, sec-butyl, tertiarybutyl and the like. The compound of formula (1) wherein $R_1$, $R_2$, $R_3$ and $R_4$ are each tertiarybutyl, or 4,4'-bis(2,6-di-tertiarybutyl-phenol), is preferred in the method of use according to the present invention.

As used herein, the term "patient" refers to warm-blooded animals or mammals, including humans, who are afflicted with diabetes mellitus, IDDM or NIDDM, as either a primary or as a secondary disease state. Treatment of a patient afflicted with diabetes mellitus refers to the reduction of the patient's blood glucose levels.

Diagnosis of patients afflicted with diabetes mellitus is well within the ability and knowledge of one skilled in the art. For example, individuals who have symptoms of polydipsia, polyuria, polyphagia and weight loss coupled with an elevation of plasma glucose over normal levels are generally considered within the diagnosis of diabetes mellitus. A clinician skilled in the art can readily identify, by the use of clinical tests, physical examination and medical/family history, those patients who are afflicted with diabetes mellitus.

A therapeutically effective glucose lowering amount of a compound of formula (1) is that amount, either in single or in multiple doses, which is effective in significantly reducing plasma glucose levels in a patient afflicted with diabetes mellitus. An effective dose can be readily determined by the use of conventional techniques and by observing results obtained under analogous circumstances. In determining the effective dose, a number of factors are considered including, but not limited to: the patient's size, age, and general health; the degree of or involvement or the severity of the disease; the response of the individual patient; the particular compound administered; the mode of administration; the bioavailability characteristics of the preparation administered; the dose regimen selected; and the use of concomitant medication.

A therapeutically effective glucose lowering amount of a compound of formula (1) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the severity of the disease and other relevant circumstances.

Compounds of the present invention can be administered in the form of pharmaceutical compositions or medicaments which are made by combining compounds of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, compounds of the present invention may be incorporated with excipients and used in the form of tablets, troches, capsules, elixirs, suspensions, syrups, wafers, chewing gums and the like. These preparations should contain at least 4% of the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of the present invention may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

In the end use application provided by the present invention, the preferred compound of formula (1) is 4,4'-bis(2,6-di-tertiarybutyl-phenol). Compounds of the present invention, including 4,4'-bis(2,6-di-tertiarybutyl-phenol), have been disclosed by S. Lerner [U.S. Pat. No. 4,115,590, issued 9/19/78] as being effective in reducing levels of plasma lipid, including cholesterol, phospholipid and triglyceride.

The compounds of the present invention, including 4,4'-bis(2,6-di-tertiarybutyl phenol), can be made according to procedures which are well known and appreciated in the art such as by a reduction of the corresponding diphenoquinone intermediate. For example, Kharasch and Jashi have described a method of reducing 3,3',5,5'-tetra-tertiarybutyl-diphenoquinone to 4,4'-bis(2,6-di-tertiarybutyl-phenol) using sodium hydrosulfite as the reducing agent [*J. Org. Chem.* 22, 1439 (1957)].

The 3,3',5,5'-tetra-alkyl-diphenoquinone intermediate can be prepared from the corresponding 2,6-dialkylphenol by procedures which are also well known and appreciated in the art. For example, Hart and Cassis [*J. Amer. Chem. Soc.* 73, 3179 (1951)] describe a nitric acid catalyzed oxidative coupling of 2,6-di-tertiarybutyl-phenol to yield 3,3',5,5'-tetra-tertiarybutyl-diphenoquinone. Furthermore, Pastor [*J. Org. Chem.* 49, 5260 (1984)] has described a 2-step synthesis of 3,3',5,5'-tetra-tertiarybutyl-diphenoquinone from 2,6-di-tertiarylbutylphenol involving formation of bis(3,5-di-tertiarybutylphenyl)disulfide by reacting 2,6-di-tertiarybutyl-phenol with $S_2Cl_2$ in the presence of $TiCl_3$ and further reacting the disulfide thus formed with chlorine (gas) followed by treatment with N,N-diethylethanamine.

In addition, the present invention provides a novel process of making the compounds useful in the present invention comprising the steps of (a) reacting compounds of the formulae

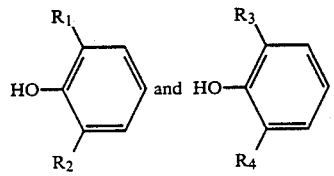

wherein $R_1$, $R_2$, $R_3$ and $R_4$ are each independently a $C_1$-$C_6$ alkyl group, with a ferricyanide salt in the presence of a base of an alkali earth metal, and (b) reducing the 3,3',5,5'-tetra-alkyl-diphenoquinone thus formed with zinc in the presence of an organic acid.

In step (a), the dialkylphenol undergoes an oxidative coupling reaction catalyzed by the ferricyanide salt in the presence of a strong base of an alkali earth metal such as KOH, NaOH, $K_2CO_3$, $Na_2CO_3$ and the like. KOH is the preferred base for use in the oxidative coupling step. The term "ferricyanide salt" refers to an alkali earth metal salt of the ferricyanide anion $-^3Fe(CN)_6$ such as $Na_3Fe(CN)_6$, $K_3Fe(CN)_6$ and the like. The preferred ferricyanide salt for use in the process of the present invention is $K_3Fe(CN)_6$. Generally, the ferricyanide salt and the alkali earth metal base are selected so as to have the same cation.

The ferricyanide salt should be present in the reaction mixture in an amount at least equimolar to that of the dialkylphenol or, more preferably, at least 2 times the molar amount of the dialkylphenol. Most preferably, the ferricyanide salt should be present in the reaction mixture in an amount of from about 2 to about 3 times the molar amount of the dialkylphenol. In addition, the base of an alkali earth metal should be present in the reaction mixture in an amount of from about 0.5 to about 5 times the molar amount of the dialkylphenol, and preferably in an amount of from about 2 to about 3 times the molar amount of the dialkylphenol.

In step (b), the 3,3',5,5'-tetra-alkyl-diphenoquinone formed in step (a) is converted to the corresponding bisphenol by a zinc reduction in the presence of an organic acid, such as acetic acid and the like. Acetic acid is preferred as the medium for step (b).

The zinc dust should be in at least a 2-fold molar excess over that of the 3,3',5,5'-tetra-alkyl-diphenoquinone, and preferably in a 3 to 5-fold excess. The reaction can generally carried out in an organic acid medium such as in acetic acid. Sufficient organic acid should be present in order to dissolve the 3,3',5,5'-tetra-alkyl-diphenoquinone.

Of course it will be recognized by those skilled in the art that symmetrical bisphenols (wherein $R_1$, $R_2$, $R_3$ and $R_4$ are each the same group) and unsymmetrical bisphenols (wherein $R_1$, $R_2$, $R_3$ and $R_4$ are not each the same group) can be prepared by the process of the present invention. Where a symmetrical bisphenol is desired, a single 2,6-di-alkyl-phenol is used as the starting material. Where an unsymmetrical bisphenol is desired, an equimolar mixture of the appropriate 2,6-di-alkyl-phenols are utilized as the starting material and the desired product is isolated from the resulting mixture of bisphenols. The preferred use of the process of the present invention, however, is in making symmetrical bisphenols such as 4,4'-bis(2,6-di-tertiarybutyl-phenol).

The following examples illustrate the preparation and use of 4,4'-bis(2,6-di-tertiarybutyl-phenol). These examples are illustrative only and are not intended to limit the scope of the invention in any way.

EXAMPLE 1

Preparation of 4,4'-Bis(2,6-di-tertiarybutyl-phenol)

Step (a): Stir a solution of potassium ferricyanide [45.3 grams (g), 0.138 moles (mol)] and potassium hydroxide (8.4 g, 0.150 mol) in 200 milliliters (mL) of water under positive nitrogen pressure for 1/2 hour. Add a solution of 2,6-ditertiarybutyl-phenol (11.3 g, 0.055 mol) in 100 mL of diethyl ether and stir the reaction mixture under positive nitrogen pressure for 5 hours. Dilute the mixture with water, diethyl ether and tetrahydrofuran and separate the organic layer. Wash the organic layer 3 times with water and evaporate the organic solvent under reduced pressure to yield 3,3'5,5'-tetratertiarybutyl-diphenoquinone (11.0 g).

Step (b): To 3,3'5,5'-tetra-tertiarybutyl-diphenoquinone (11.0 g) add 200 mL of acetic acid and stir the solution at ambient temperature. Add zinc dust (7.0 g) to the solution and heat the mixture to reflux with stirring for 1 hour. Filter the mixture and wash the precipitate with diethyl ether. Dilute the combined filtrate with water and separate the organic layer. Wash the organic layer 3 times with water and once with saturated $NaHCO_3$. Filter the organic layer through $Na_2SO_4$ and evaporate the organic solvent to yield the title compound (11.3 g). Recrystallize the product from hexane to yield the purified title compound (9.8 g, 87% overall yield).

Light yellow crystals, melting point = 183°–84° C.

EXAMPLE 2

Hypoglycemic Effect of 4,4'-Bis(2,6-di-tertiarybutyl-phenol) in Alloxan-Treated Rats Normal male, Sprague-Dawley, rats of comparable weight and age are assigned to one of three groups and are treated as follows:

1. Non diabetic control—10 animals receive rat chow for two weeks;
2. Diabetic control—25-30 animals receive rat chow for two weeks;
3. Bisphenol—25-30 animals receive rat chow containing 4,4'-bis(2,6-di-tertiarybutyl-phenol), 1% (w/w), for two weeks.

At the end of the 2 week treatment, animals in groups 2 and 3 receive a single dose of alloxan (40 milligrams/kilogram of body weight) by intravenous administration and animals in group 1 receive a comparable dose of saline. Animals continue to receive the diet indicated for their group for an additional 5 days. On the fifth day after alloxan or saline treatment, urine is collected for 4 hours and analyzed for glucose. Animals are then fasted overnight and are sacrificed by exsanguination under metophane anesthesia. Blood plasma samples are analyzed for glucose, triglycerides and insulin. Pancreases are collected for histological examination.

The results of this study, presented in Table 1, clearly show that treatment with 4,4'-bis(2,6-di-tertiarybutyl-phenol) significantly reduces blood glucose in rats with alloxan-induced diabetes as compared to the diabetic controls.

TABLE 1

| Effect of 4,4'-Bis(2,6-di-tertiarybutyl-phenol) in Alloxan-Treated Rats | | | | |
|---|---|---|---|---|
| Treatment group | Urine Glucose (mg/4 hr) | Plasma Glucose (mg/dl) | Triglycerides (mg/dl) | Insulin ($\mu$U/ml) |
| Nondiabetic Control | None | 128 ± 11$^{a*}$ | 14 ± 3* | 47 ± 19* |
| Diabetic Control | 1.2 ± 0.4 | 364 ± 120 | 140 ± 149 | 29 ± 12 |
| Bisphenol | 0.39 ± 4* | 135 ± 58* | 17 ± 9* | 23 ± 4 |

$^a$Mean values ± standard deviation
*p ≤ .05 as compared to Diabetic Control

We claim:

1. A process of making a compound of the formula

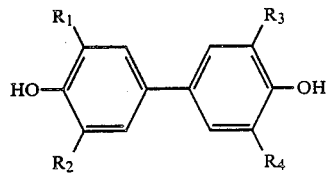

wherein $R_1$, $R_2$, $R_3$ and $R_4$ are each independently a $C_1$-$C_6$ alkyl group, comprising the steps of
   (a) reacting 2,6-di-alkylphenols of the formulae

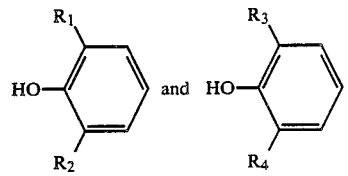

wherein $R_1$, $R_2$, $R_3$ and $R_4$ are each independently a $C_1$-$C_6$ alkyl group, with a ferricyanide salt in the presence of a base selected from the group consisting of KOH, NaOH, $K_2CO_3$ and $Na_2CO_3$, and
   (b) reducing the 3,3',5,5'-tetra-alkyl-diphenoquinone thus formed with zinc in the presence of acetic acid at about reflux temperature.

* * * * *